United States Patent
Bix

(10) Patent No.: US 9,370,547 B2
(45) Date of Patent: Jun. 21, 2016

(54) COMPOSITIONS AND METHODS FOR TREATING ISCHEMIA

(71) Applicant: UNIVERSITY OF KENTUCKY RESEARCH FOUNDATION, Lexington, KY (US)

(72) Inventor: Gregory Bix, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 14/620,013

(22) Filed: Feb. 11, 2015

(65) Prior Publication Data

US 2015/0224165 A1 Aug. 13, 2015

Related U.S. Application Data

(60) Provisional application No. 61/938,621, filed on Feb. 11, 2014.

(51) Int. Cl.
*A61K 38/08* (2006.01)
*A61K 38/39* (2006.01)

(52) U.S. Cl.
CPC .............. *A61K 38/08* (2013.01); *A61K 38/39* (2013.01)

(58) Field of Classification Search
None
See application file for complete search history.

(56) References Cited

PUBLICATIONS

Fondevila et al. "Cyclic RGD Peptides With High Affinity for alpha5beta1 Integrin Protect Genetically Fat Zucker Rat Livers From Cold Ischemia/Reperfusion Injury," Transplantation Proceedings, 37, 1679-1681 (2005).*
Lee B, Clarke D, Al Ahmad A, Kahle M, Parham C, Auckland L, et al. Perlecan domain v is neuroprotective and proangiogenic following ischemic stroke in rodents. The Journal of Clinical Investigation. 2011;121:3005-3023.
Bix GJ. Perlecan and the blood-brain barrier: Beneficial proteolysis? Brain Res. 2012;3:155.
Saini M, Pinteaux E, Lee B, Bix G. Oxygen-glucose deprivation and interleukin-1a trigger the release of perlecan Ig3 by cells of neurovascular unit. J Neurochem. 2011;119:760-771.
Al-Ahmad AJ, Lee B, Saini M, Bix GJ. Perlecan domain v modulates astrogliosis in vitro and after focal cerebral ischemia through multiple receptors and increased nerve growth factor release. Glia. 2011;59:1822-1840.
Bix G, Gowing E, Clarkson A. Perlecan domain v is neuroprotective and affords functional improvement in a photothrombotic stroke model in young and aged mice. Translational Stroke Research. 2013;4:515-523.
Clarke DN, Al Ahmad A, Lee B, Parham C, Auckland L, Fertala A, et al. Perlecan domain v induces vegf secretion in brain endothelial cells through integrin a5b1 and erk-dependent signlaing pathways. PLOS One. 2012;epub ahead of print:445257.
Li L, Liu F, Welser-Alves JV, McCullough LD, Milner R. Upregulation of fibronectin and the a5131 and av133 integrins on blood vessels within the cerebral ischemic penumbra. Experimental Neurology. 2012;233:283-291.
Li L, Welser-Alves J, van der Flier A, Boroujerdi A, Hynes RO, Milner R. An angiogenic role for the a5131 integrin in promoting endothelial cell proliferation during cerebral hypoxia. Experimental Neurology. 2012;237:46-54.
Veine D, Yao H, Stafford D, Fay K, Livant D. A d-amino acid containing peptide as a potent, noncovalent inhibitor of a5131 integrin in human prostate cancer invasion and lung colonization. Clinical & Experimental Metastasis. 2014;31:379-393.
Shimamura N, Matchett G, Solaroglu I, Tsubokawa T, Ohkuma H, Zhang J. Inhibition of integrin av133 reduces blood-brain barrier breakdown in focal ischemia in rats. Journal of Neuroscience Research.2006;84:1837-1847.
Shimamura N, Matchett G, Yatsushige H, Calvert JW, Ohkuma H, Zhang J. Inhibition of integrin av133 ameliorates focal cerebral ischemic damage in the rat middle cerebral artery occlusion model. Stroke. 2006;37:1902-1909.
Osada T, Gu Y-H, Kanazawa M, Tsubota Y, Hawkins BT, Spatz M, et al. Interendothelial claudin-5 expression depends on cerebral endothelial cell-matrix adhesion by [beta]1-integrins. J Cereb Blood Flow Metab. 2011;31:1972-1985.
Danese S, Sans M, Spencer DM, Beck I, Donate F, Plunkett ML, et al. Angiogenesis blockade as a new therapeutic approach to experimental colitis. Gut. 2007;56:855-862.
Bix G, Fu J, Gonzalez E, Macro L, Barker A, Campbell S, et al. Endorepellin causes endothelial cell disassembly of actin cytoskeleton and focal adhesions through the α2β1 integrin. J.Cell Biol. 2004;166:97-109.
Saini MG, Bix GJ. Oxygen—glucose deprivation (ogd) and interleukin-1 (il-1) differentially modulate cathepsin b/l mediated generation of neuroprotective perlecan Ig3 by neurons. Brain Research. 2012;1438:65-74.

* cited by examiner

*Primary Examiner* — Christina Bradley
(74) *Attorney, Agent, or Firm* — Stites & Harbison PLLC; Mandy Wilson Decker

(57) ABSTRACT

The presently-disclosed subject matter provides methods for preventing ischemia in a cell, treating ischemia in a subject, and preventing an infarction in a subject that utilize α5β1 integrin inhibitor. In some instances, α5β1 integrin inhibitor is administered to a subject prior to, during, or after the onset of ischemia to treat the ischemia and/or prevent infarction. In some instances the present methods prevent the occurrence of an infarction. In some instances the present methods restores perfusion to organs and tissues.

12 Claims, 11 Drawing Sheets

WB: Claudin-5

US 9,370,547 B2

SEQUENCE LISTING

<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: Synthesized

<400> SEQUENCE: 1

Cys Arg Arg Glu Thr Ala Trp Ala Cys
1               5

COMPOSITIONS AND METHODS FOR TREATING ISCHEMIA

RELATED APPLICATIONS

This application claims the benefit of U.S. Provisional Patent Application No. 61/938,621, filed Feb. 11, 2014, the entire disclosure of which is hereby incorporated by reference.

GOVERNMENT INTEREST

This invention was made with government support under Grant No. 2Rβ1NS065842-08 the awarded by the National Institutes of Health. The government has certain rights in the invention.

TECHNICAL FIELD

The presently-disclosed subject matter relates to the treatment of ischemia, including cerebral ischemia and stroke. In particular, embodiments of the presently-disclosed subject matter relate to methods for preventing and/or treating ischemia and potential infarction that utilize an α5β1 integrin inhibitor.

INTRODUCTION

Tissues deprived of blood and oxygen undergo ischemic necrosis or infarction with possible irreversible organ damage. Cerebral ischemia results from decreased blood and oxygen flow implicating one or more of the blood vessels of the brain. In cerebral ischemia, the individual suffers a stroke with sudden development of a focal neurologic deficit and, in most cases, some degree of brain damage. The decreased blood flow may be due to, for example, an occlusion such as a thrombus or embolus, vessel rupture, sudden fall in blood pressure, change in the vessel lumen diameter due to atherosclerosis, trauma, aneurysm, developmental malformation, altered permeability of the vessel wall or increased viscosity or other quality of the blood. Decreased blood flow may also be due to failure of the systemic circulation and severe prolonged hypotension. Ischemic necrosis of the spinal cord may result in sensory or motor symptoms or both that can be referred to cervical, thoracic or lumbar levels of the spine.

Current treatments for ischemia encompass behavioral changes, drug therapy, and/or surgical intervention. Drugs are frequently preferred before resorting to invasive procedures and to provide more immediate relief than long-term behavioral changes. However, current drugs are limited in their effectiveness in preventing infarction.

Similarly, stroke is the fourth leading cause of death in the U.S., and approximately 87% of stroke patients are ischemic, resulting from a lack of blood flow to a part of the brain. Current standard of care for ischemic stroke is rapid reopening of the occluded brain blood vessel with tissue plasminogen activator (t-PA). Unfortunately, t-PA is limited to a brief window of 4.5 hours within symptom onset contributing, along with other factors, to the exclusion of many patients. Furthermore, results from large t-PA trials have been mixed, showing improving recanalization rates, but no overwhelming improvements in outcome.

Thus, there is a need for a therapeutic agent which can be useful in treating ischemia as well as associated infarction and cell death.

DESCRIPTION OF THE DRAWINGS

Illustrative aspects of embodiments of the present invention will be described in detail with reference to the following figures wherein.

DESCRIPTION OF EXEMPLARY EMBODIMENTS

Figure 1A:
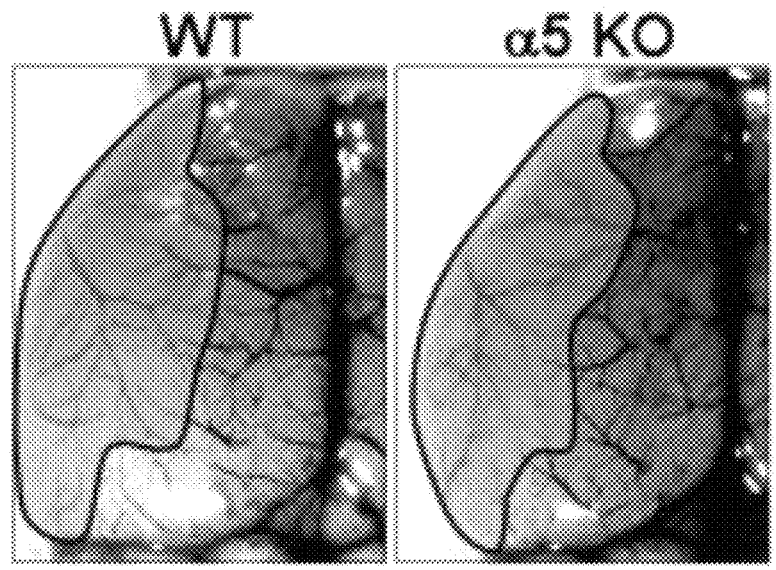
FIG. 1A includes images of brains where carbon black ink was injected into the cerebral vasculature showing the left hemisphere, where the shaded region indicates the territory of the middle cerebral artery (MCA).

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding, and no unnecessary limitations are to be understood therefrom.

The presently disclosed subject matter is directed to preventing and/or treating ischemia with methods that involve use of an α5β1 integrin inhibitor. As is known in the art, ischemia can lead to infarction in a subject. Therefore, the presently-disclosed subject matter further relates to methods for preventing and/or treating an infarction in a subject, and such methods involve the use of an α5β1 integrin inhibitor.

In some embodiments, a method is provided for preventing ischemia in a cell, wherein the ischemia may be caused by one or more ischemic events. In some embodiment the method includes contacting the cell with an α5β1 integrin inhibitor. The term "contacting" as used herein refers to any means by which an α5β1 integrin inhibitor brought into sufficient proximity and/or in direct contact with a cell such that the cell is capable of receiving the α5β1 integrin inhibitor. For instance, in some embodiments contact refers to coating a cell with an α5β1 integrin inhibitor. In other embodiments contact refers to culturing a cell in a solution that includes an α5β1 integrin inhibitor. In other embodiments the cell is within a subject, and contact refers to administering an α5β1 integrin inhibitor to the subject such that a cell within the subject is capable of receiving an α5β1 integrin inhibitor.

The term "preventing" as used herein refers to the characteristic of reducing or eliminating ischemia as well as the side effects associated with ischemia, which can include infarction. The term "preventing" does not imply a particular degree of reduction or elimination of ischemia. Likewise, the term "preventing" does not imply that infarction due to ischemia is eliminated. Instead, the term "preventing" refers to reducing ischemia as well as side effects thereof, including potentially infarction, by about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% relative to a control that has not been contacted or treated with an α5β1 integrin inhibitor.

Furthermore, the terms "inhibitor" and the like do not necessarily refer to the ability to completely inactivate all target biological activity in all cases. Rather, the skilled artisan will understand that the term "inhibitor" refers to a substance that can decrease biological activity of a target, such as can occur with a ligand binding site of the target, or protein in a biochemical pathway of the target is blocked, or when a non-native complex with the target, or protein in a biochemical pathway of the target, is formed. Such decrease in biological activity can be determined relative to a control, wherein an inhibitor is not administered and/or placed in contact with the target. Accordingly, the term "α5β1 integrin inhibitor" refers to substances that can decrease or eliminate α5β1 integrin activity, optionally relative to a control that has not been contacted with an α5β1 integrin inhibitor. In some embodiments, a decrease in α5β1 integrin activity relative to a control can be about a 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% decrease.

In some embodiments, the α5β1 integrin inhibitor is selected from small molecule and a polypeptide.

As used herein, the term "polypeptide" means any polymer comprising any of the 20 protein amino acids, regardless of its size. Although "protein" is often used in reference to relatively large polypeptides, and "peptide" is often used in reference to small polypeptides, usage of these terms in the art overlaps and varies. The term "polypeptide" as used herein refers to peptides, polypeptides and proteins, unless otherwise noted. As used herein, the terms "protein," "polypeptide," and "peptide" are used interchangeably herein when referring to a gene product. Unless otherwise indicated, a particular polypeptide also implicitly encompasses conservatively-substituted variants thereof.

As used herein, "small molecule" refers to a non-peptidic, non-oligomeric organic compound either synthesized in the laboratory or found in nature. Small molecules, as used herein, can refer to compounds that are "natural product-like," however, the term "small molecule" is not limited to "natural product-like" compounds. Rather, a small molecule is typically characterized in that it possesses one or more of the following characteristics including having several carbon-carbon bonds, having multiple stereocenters, having multiple functional groups, having at least two different types of functional groups, and having a molecular weight of less than 1500, although this characterization is not intended to be limiting for the purposes of the disclosure.

In some embodiments the α5β1 integrin inhibitor is selected from ATN-161, Ac-PhScN—NH$_2$, CRRETAWAC (SEQ. ID NO: 1) α5β1 integrin inhibitor peptide, and combinations thereof. ATN-161 is a peptide with the amino acid sequence PHSCN that has been developed to inhibit α5β1 integrin and has successfully completed Phase I and Phase II clinical trials for recurrent intracranial malignant glioma. Among other things, ATN-161 can be safely administered intravenously, has a relatively short serum half-life (e.g., 3-5 h for some subjects) with high tissue distribution, and localizes to vasculature over-expressing activated, but not unactivated, α5β1 integrin. ATN-161, in addition to noncovalent interaction with the α5 integrin subunit, can have a covalent interaction with the β1 and β3 subunit of α5β1 and αvβ3 integrin.

Ac-PhScN—NH$_2$ is a modified version of ATN-161 in which the covalent interaction is eliminated by replacing the H and C with D-stereoisomers. Ac-PhScN—NH$_2$ specifically and noncovalently interacts with the α5 subunit of α5β1 integrin and is between 27,000 fold and 379,000 fold more potent and specifically inhibits activated α5β1 integrin mediated processes.

In some embodiments the α5β1 integrin inhibitor includes a CRRETAWAC α5β1 integrin inhibitor peptide. See, e.g., Koivunen E, Wang B, Ruoslahti E. Isolation of a highly specific ligand for the alpha 5 beta 1 integrin from a phage display library. *J Cell Biol.* 1994; 124(3):373-380. In some embodiments the α5β1 integrin inhibitor is selected from an α5β1 integrin antibody that inhibits the function of the α5β1 integrin inhibitor. Those of ordinary skill in the art will recognize antibodies for blocking the function of α5β1 integrin, as well as such antibodies suited for use in particular subjects, including human and non-human subjects.

Additionally, without being bound by theory or mechanism, relatively small peptides such as ATN-161, Ac-PhScN—NH2 and CRRETAWAC (SEQ ID NO: 1) α5β1 integrin inhibitor peptide may not be able to cross the intact blood-brain barrier (BBB), like other small peptides cannot. This characteristic can be advantageous for targeting circulation accessible activated brain endothelial cell α5β1 integrin to potentially stabilize the BBB.

With respect to methods for preventing ischemia in a cell, in some embodiments the cell is a brain cell. In other embodiments the cell is part of a particular tissue, and the method includes preventing ischemia in the cell(s) of the tissue. In this respect, the term "tissue" is used herein to refer to a population of cells, generally consisting of cells of the same kind that perform the same or similar functions. The types of cells that make the tissue are not limited. In some embodiments tissue is part of a living organism, and in some embodiments tissue is tissue excised from a living organism or artificial tissue. In some embodiments tissue can be part of an organ, wherein the term "organ" refers to a part of a subject which is composed of several tissues and adapted to perform a specific function or functions, such as the brain.

The presently-disclosed subject matter also relates to methods for treating ischemia in a subject. In some embodiments the method comprises administering to the subject an effective amount of an α5β1 integrin inhibitor. In some embodiments the α5β1 integrin inhibitor is selected from small molecule and a polypeptide. In some embodiments the α5β1 integrin inhibitor is selected from ATN-161, Ac-PhScN—NH$_2$ CRRETAWAC (SEQ ID NO: 1) α5β1 integrin inhibitor peptide, and combinations thereof.

The term "administering" refers to any method of providing an α5β1 integrin inhibitor and/or pharmaceutical composition thereof to a subject. Such methods are well known to those skilled in the art and include, but are not limited to, oral administration, transdermal administration, nasal administration, intracerebral administration, and administration by injection, which itself can include intravenous administration, intra-arterial administration, intramuscular administration, subcutaneous administration, intravitreous administration, intracameral (into anterior chamber) administration, and the like. Administration can be continuous or intermittent. In various aspects, a preparation can be administered therapeutically; that is, administered to treat an existing disease or condition (e.g., ischemia, infarction, etc.). In other instances a preparation is administered prophylactically; that is, administered to prevent or treat a disease or condition that may otherwise develop.

As used herein, the terms "effective amount" and "therapeutically effective amount" are used interchangeably and mean a dosage sufficient to provide treatment. The exact amount that is required will vary from subject to subject, depending on the species, age, and general condition of the subject, the particular carrier or adjuvant being used, mode of administration, and the like. As such, the effective amount will vary based on the particular circumstances, and an appropriate effective amount can be determined in a particular case by one of ordinary skill in the art using only routine experimentation.

In some instances an effective amount is determined relative to the weight of a subject, and can be selected from dosages of about 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg, 31 mg/kg, 32 mg/kg, 33 mg/kg, 34 mg/kg, 35 mg/kg, 36 mg/kg, 37 mg/kg, 38 mg/kg, 39 mg/kg, 40 mg/kg, 41 mg/kg, 42 mg/kg, 43 mg/kg, 44 mg/kg, 45 mg/kg, 46 mg/kg, 47 mg/kg, 48 mg/kg, 49 mg/kg, and 50 mg/kg.

The term "subject" is used herein to refer to a target of administration, which optionally displays symptoms related to a particular disease, pathological condition, disorder, or the like. Thus, in some embodiments a subject refers to a target that displays symptoms of ischemia and/or infarction. The subject of the herein disclosed methods can include both human and animal subjects. A subject can be, but is not limited to, vertebrates, such as mammals, fish, birds, reptiles, or amphibians. More specifically, the subject of the herein disclosed methods can include, but is not limited to, a human, non-human primate, cat, dog, deer, bison, horse, pig, rabbit, dog, sheep, goat, cow, cat, guinea pig, or rodent. The term does not denote a particular age or sex. Adult and newborn subjects, as well as fetuses, whether male or female, are intended to be covered. The term "subject" includes human and veterinary subjects.

The terms "treat," "treatment," and the like refer to the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative (prophylatic) treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

In some methods for treating ischemia, the ischemia is caused by a particular ischemic event. In some instances, the ischemia is caused at least in part by an ischemic event selected from cerebral ischemia, stroke, and a combination thereof. In some embodiments the α5β1 integrin inhibitor is administered one or more times during or after the onset of ischemia and/or during or after an ischemic event. In this respect, in some embodiments an α5β1 integrin inhibitor is administered one or more times during or after the onset of two or more distinct ischemic events, and therefore the present methods are not limited to a single administration of an α5β1 integrin inhibitor. In such embodiments, the α5β1 integrin inhibitor can optionally be administered about 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 hours after the onset of the ischemic.

As discussed above, treatment can be preventative (prophylactic) in some instances. Accordingly, in some embodiments of the presently-disclosed treatment methods, the α5β1 integrin inhibitor is administered prior to the onset of ischemia and/or prior to an ischemic event. In some embodiments the α5β1 integrin inhibitor is administered prior to each of one or more separate onsets of ischemia and/or ischemic events.

In some embodiments administration of an α5β1 integrin inhibitor to a subject, prior to, during, and/or after the onset of ischemia, can prevent (i.e., 1-100% reduction relative to control) the occurrence of infarction in the subject. Alternatively or additionally, in some embodiments administration of an α5β1 integrin inhibitor to a subject, prior to, during, and/or after the onset of ischemia, can restore perfusion to tissues and organs in the subject.

Further still, the presently-disclosed subject matter relates to methods for preventing an infarction in a subject. In some embodiments, a method for preventing an infarction in a subject comprises administering an effective amount of an α5β1 integrin inhibitor. In some embodiments the α5β1 integrin inhibitor is selected from small molecule and a polypeptide. In some embodiments the α5β1 integrin inhibitor is selected from ATN-161, Ac-PhScN—NH₂ CRRETAWAC (SEQ ID NO: 1) α5β1 integrin inhibitor peptide, and combinations thereof.

In some embodiments of methods for preventing an infraction in a subject, prior to administering an α5β1 integrin inhibitor, the subject is first diagnosed and/or prognosed as having ischemia. In some instances the subject can be diagnosed as having ischemia that has already led to an infarction in the subject. Administration of an α5β1 integrin inhibitor prior to an ischemic event, whether or not a subject has been prognosed as being at risk for ischemia, could therefore serve as a preventative treatment for ischemia, and potentially infarction.

The terms "diagnose" and the like as used herein refer to methods by which the skilled artisan can estimate and even determine whether or not a subject is suffering from a given disease or condition, such as ischemia. Along with diagnosis, clinical "prognosis" or "prognosticating" is also an area of great concern and interest, and the terms "prognose" and the like refer to act of determining the relative risk associated with particular conditions in order to plan the most effective therapy. If an accurate prognosis can be made, appropriate therapy, and in some instances less severe therapy or more effective therapy, for the subject can be chosen. For instance, in some embodiments of the presently disclosed subject matter, a subject that is prognosed as having ischemia can have an α5β1 integrin inhibitor administered in order to prevent the potential ischemia from developing.

Those of ordinary skill in the art will recognize factors and methods for diagnosing and/or prognosing a subject with ischemia. Factors that can contribute to a diagnosis and/or prognosis of ischemia in a subject include, but are not limited to, hypercholesterolemia, electrocardiogram (EKG) changes associated with a risk of or the presence of ischemia (e.g., peaked or inverted T-waves or ST segment elevations or depression in an appropriate clinical context), sedentary lifestyles, angiographic evidence of partial coronary artery obstruction, evidence of a cerebrovascular accident CVA, and other clinical evidence of ischemia

EXAMPLES

The presently-disclosed subject matter is further illustrated by the following specific but non-limiting examples. The examples may include compilations of data that are representative of data gathered at various times during the course of development and experimentation related to the presently-disclosed subject matter. Furthermore, some of the examples described herein may be prophetic examples.

Example 1

This Example demonstrates that stroke-induced upregulation and activation of an α5β1 integrin allows systemically administered domain V (DV) protein fragment of the brain extracellular matrix proteoglycan perlecan to target a stroke site. This Example therefore links the therapeutic effect of DV to α5β1 integrin.

A transient middle cerebral artery occlusion (MCAo) was performed in 3 month old male mice that had endothelial cell selective knockdown of the α5 integrin (referred to hereafter as "α5 integrin KO mice"). As the α5 integrin subunit is known to only heterodimerize with the β1 integrin subunit, this mouse is effectively deficient in endothelial cell α5β1 integrin. These mice were healthy, fertile, and had no spontaneous vascular or hematopoietic phenotypes, no alterations in developmental vasculogenesis or angiogenesis, no differences in vascular extracellular matrix composition or structure, and no disparities in their subsets of hematopoietic cells. Furthermore, these mice localized more αvβ3 at the brain endothelial cell surface in their focal adhesions, but exhibited no increase in total αvβ5 protein. Brain angiogenesis in the face of chronic (14 days) hypoxia was significantly delayed in these mice.

Figure 1B:
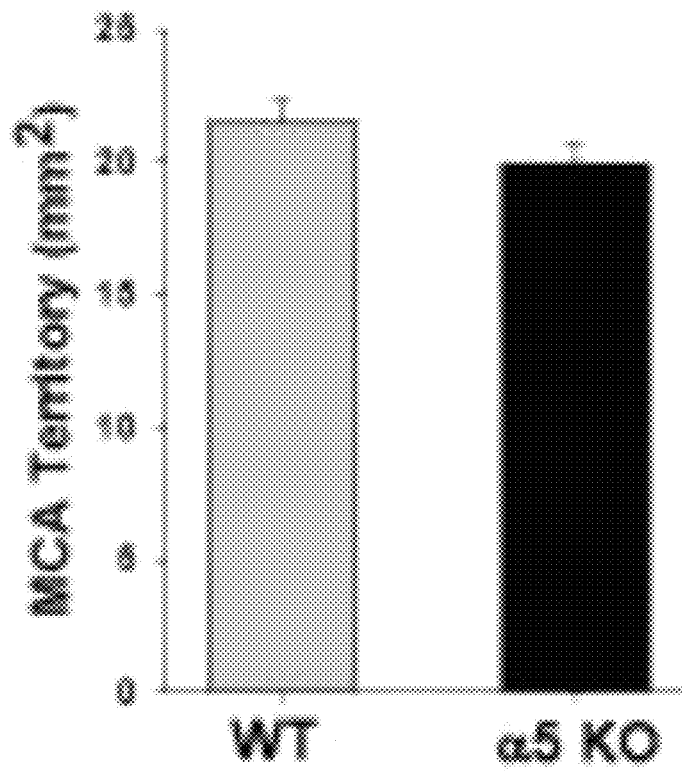
FIG. 1B includes a plot showing the quantification of MCA territory area in control and α5 KO (knockout) mice brains shown in FIG. 1A. N=6. Bars=SD.
Figure 2A:
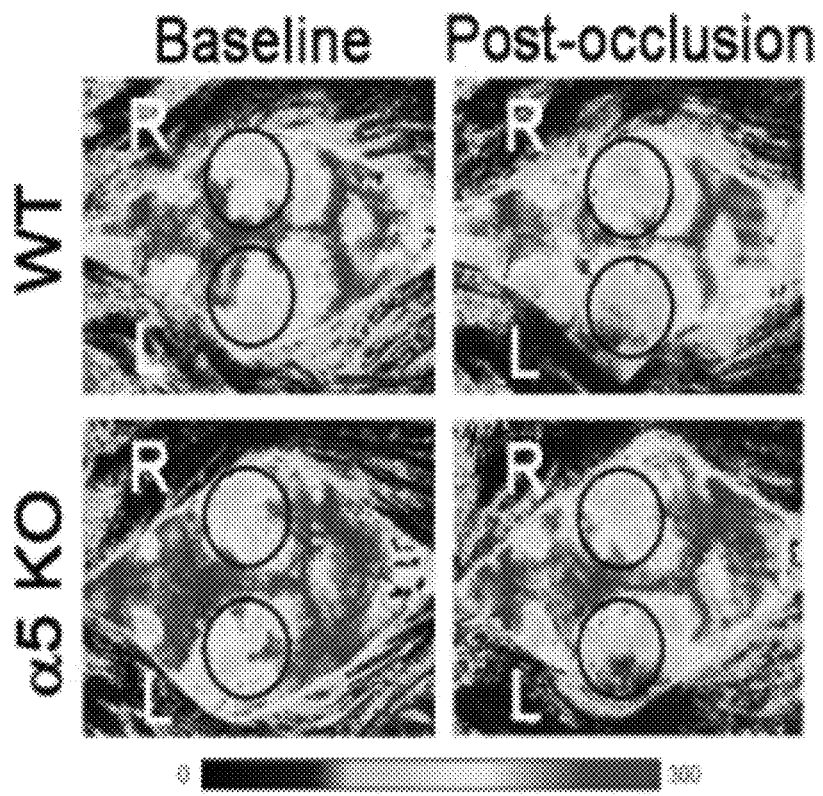
FIG. 2A includes images of laser speckle doppler flow of WT (wild type) and α5 integrin KO mice at just prior and immediately following (L)eft MCAo.
Figure 2B:
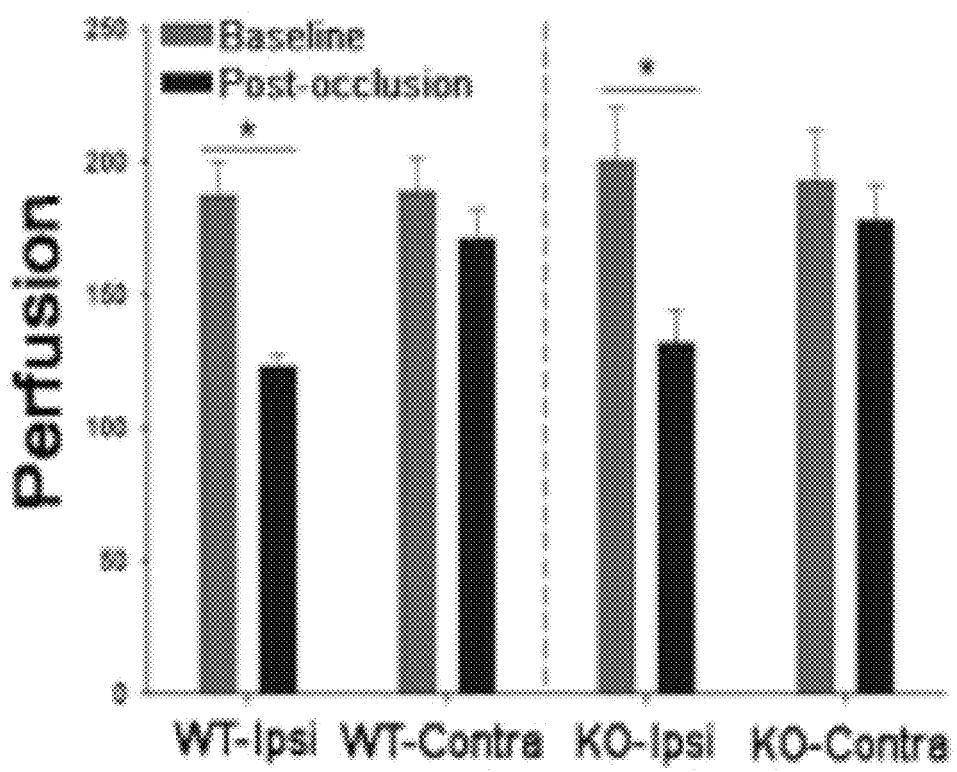
FIG. 2B includes a plot showing levels of perfusion for the samples WT and α5 integrin KO mice at just prior and immediately following (L)eft MCAo, where the data are obtained from the respective circled areas shown in FIG. 2A (N=3 animals per group, *P<0.05).

Relative to wild type (WT) littermates, analysis of the α5 integrin KO mice demonstrated no significant differences in their cerebrovascular anatomy that could otherwise explain any differences in experimental infarct size (FIGS. 1A and 1B), no significant difference in brain microvascular density as quantified by immunohistochemistry, and no significant differences in blood gas parameters. During the stroke surgery, both α5 integrin KO and WT littermates experienced similar degradations in blood flow upon MCAo as measured by laser speckle Doppler (PeriCam PSI HR, Perimed, FIGS. 2A and 2B), reducing the likelihood that potential differences in collateral circulation could account for differences in infarct size.

Figure 3A:
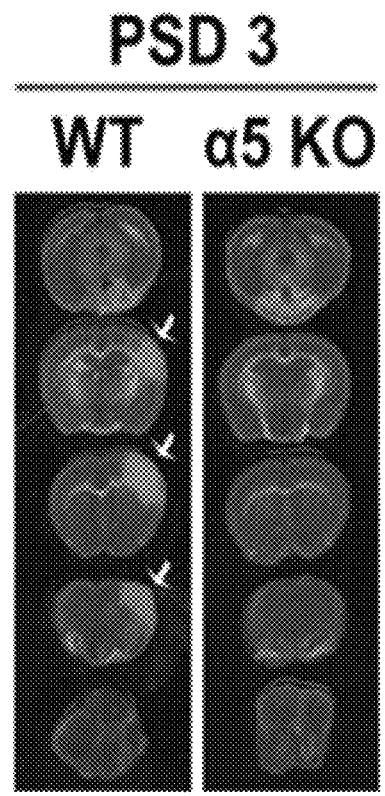
FIG. 3A includes images showing TTC in WT and α5 integrin KO mice brains 3 days after MCAo (PSD 3), where arrows indicate TTC negative areas.
Figure 3B:
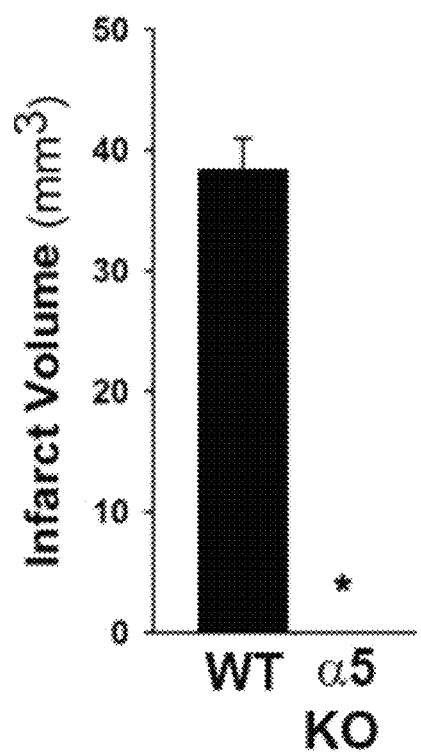
FIG. 3B includes a plot showing the quantification of mean infarct volumes of the mice brains shown in FIG. 3A (N=18 per group per PSD, 3 separate experiments, *P<0.001).
Figure 4:
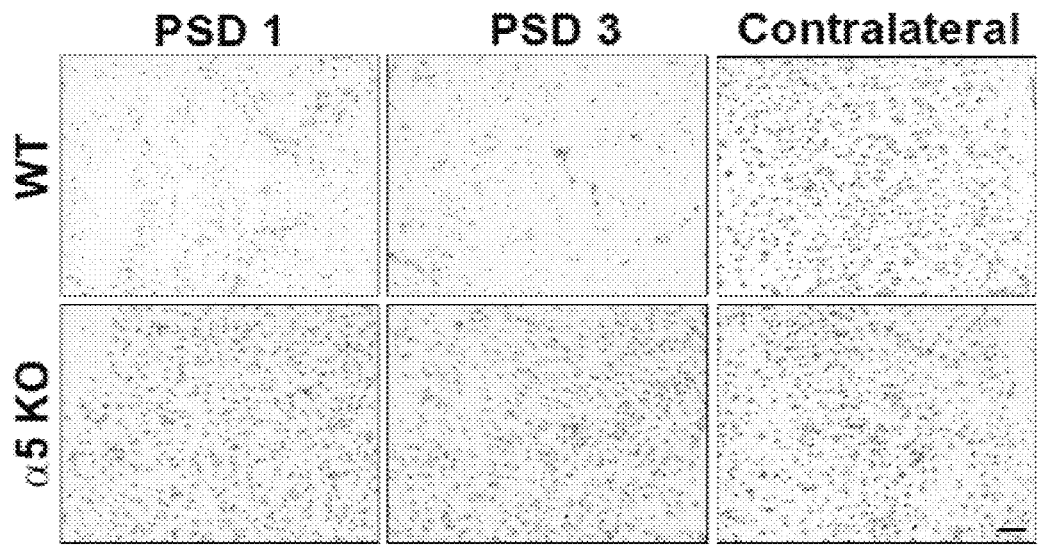
FIG. 4 includes images of a cresyl violet stain of stroke-affected and contralateral brain areas showing a significant neuronal cell dropout and pyknotic appearing neurons in WT mice but no appreciable cell dropout and relatively few pyknotic appearing neurons in α5 integrin KO mice. Scale bar=50 μm.
Figure 5:
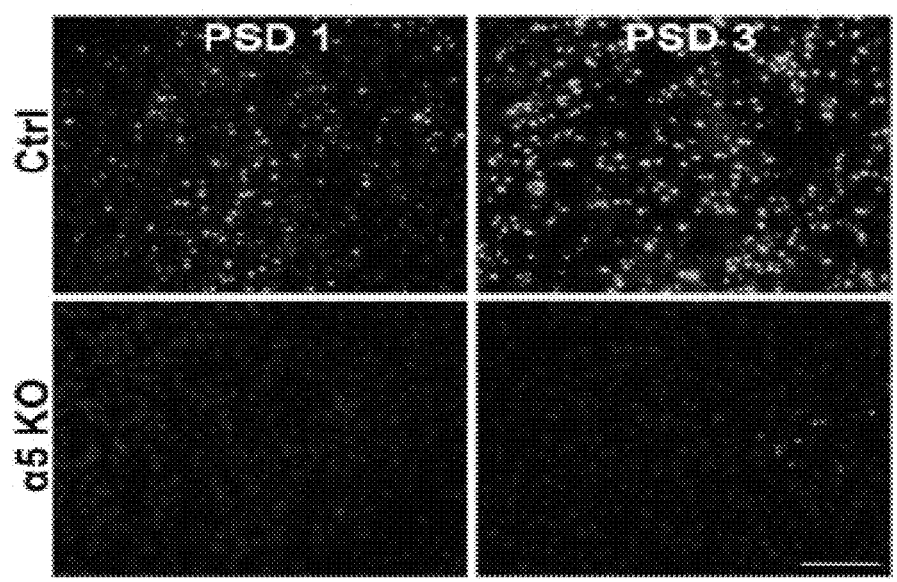
FIG. 5 includes images of TUNEL stains with DAPI nuclear counterstains of stroke-affected brain areas showing substantial and increased apoptosis in WT mice from PSD1-3 but minimal apoptosis in α5 integrin KO mice (n=3). Scale bar is 50 μm.

It was noted that the KO mice had little to no discernible infarction, as measured by (TTC) and little sign of neuronal injury (i.e., small, rounded, pyknotic appearing neurons by cresyl violet stain) or apoptotic cell death from PSD1-3 (FIGS. 3 to 5). This degree of apparent resistance to ischemic stroke injury is superior to other known genetically modified mice. The lack of neuronal injury/death was associated with a qPCR-measured decrease in the transcription of several proinflammatory cytokines (e.g. IL-1beta and TNFalpha were 0.33 fold and 0.34 fold, respectively, of PSD3 WT stroked control levels, p<0.01, n=3) and an increase in several anti-inflammatory cytokines (e.g., IL-4 and IL-10 were 131.87 fold and 25.34 more than PSD1 WT stroked control levels, p<0.001, n=3) in ipsilateral ischemic brain. These observations collectively suggest that after MCAo, α5 integrin KO mice experience a combination of less inflammation and little to no neuronal death in ischemic areas.

In this regard, one of the more prominent ways in which ischemic brain injury expands is via disruption of the blood-brain barrier (BBB), allowing for cytotoxic and vasogenic edema, infiltration of immune and inflammatory cells, and the like. For this reason, limiting poststroke BBB disruption was examined for potential therapeutic benefits. The BBB appears to open and close repeatedly after transient ischemic stroke. Typically, the hyperemia associated with reperfusion is associated with increased BBB opening, followed by a refractory period of slight hypoperfusion and a closed BBB, which is then followed by a biphasic period of BBB opening. Without being bound by theory or mechanism, the earlier periods of BBB opening may be due to increased endothelial transcytosis, while the final opening period, which typically occurs between 18-96 hours after reperfusion, is associated with increased paracellular permeability due to disruption of tight junction (TJ) proteins such as claudin-5, vasogenic edema, inflammatory cell infiltration, and the initiation of angiogenesis.

As discussed above, α5β1 integrin is a mediator in the angiogenic response, and is upregulated in stroke-affected vasculature during the first 24 hours in the MCAo model. Additionally, the difference in neuronal injury and inflammatory mediator transcription in the α5 integrin KO mice was evident as early as 24 hours post MCAo. Thus, the deletion of this single endothelial cell integrin may cause such neuroprotection by preventing the final BBB opening by stabilizing TJ proteins, thereby minimizing ischemic injury after transient MCAo.

Example 2

This Example describes procedures performed to further characterize the effect of endothelial cell selective α5β1 integrin deletion on experimental ischemic stroke.

Figure 6:
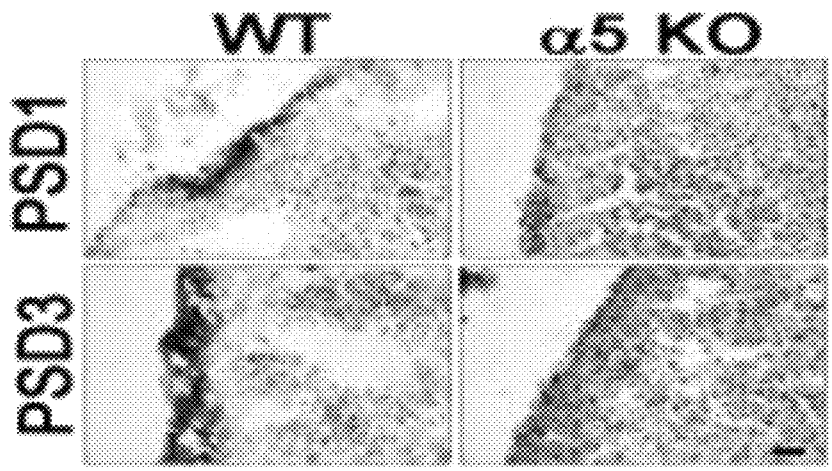
FIG. 6 includes images showing IgG (DAB stain) immunohistochemistry of stroked brain tissue on PSD 1 and 3 that were counterstained with hematoxylin. N=6. Scale bar is 50 μm.

In addition to the results detailed in Example 1 for the α5 integrin KO mice (FIGS. 1 to 5), IgG immunohistochemistry was performed to determine potential differences in post-stroke BBB permeability on PSD1 and 3 (FIG. 6). IgG immunoreactivity was abundant in all of the brains of stroked WT mice at both PSDs, but was not detected in any of the α5 integrin KO mice brains (n=6). This supports the notion that that the absence of endothelial cell α5 integrin promotes post-stroke BBB integrity.

Example 3

This Example describes procedures performed to characterize the potential of the α5β1 integrin as a therapeutic target for ischemic stroke. As discussed above, α5 integrin KO mice suggest that the α5β1 integrin could represent an effective stroke therapeutic target. In this Example, this therapeutic quality will be investigated by determining whether inhibition of the more specific α5β1 integrin in WT mice after MCAo results in resistance to ischemic injury and improved functional outcomes mirroring the results seen in stroked α5 integrin KO mice.

Figure 7A:
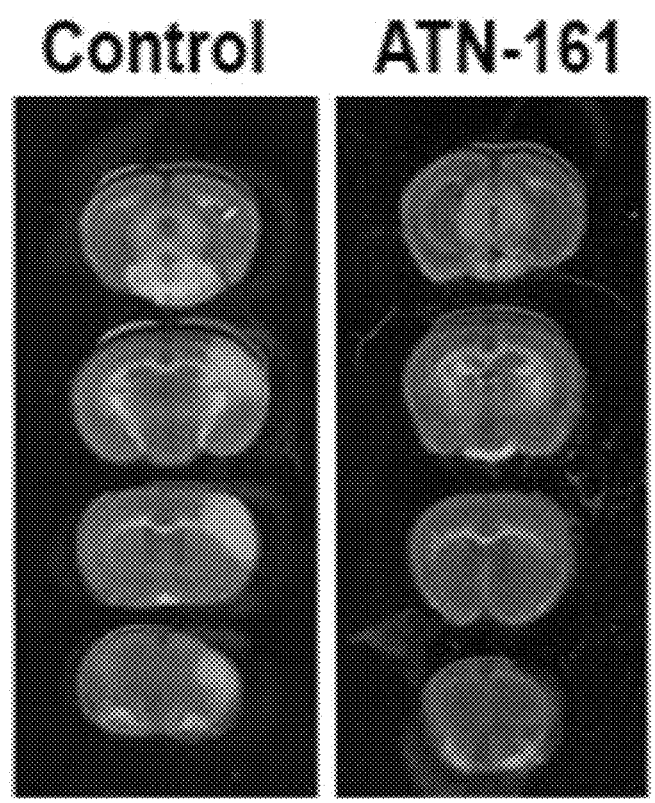
FIG. 7A includes images of PSD3 TTC stained brain sections showing WT mice treated with intravenous PBS (Control) or ATN-161 (1 mg/kg) on PSD1.
Figure 7B:
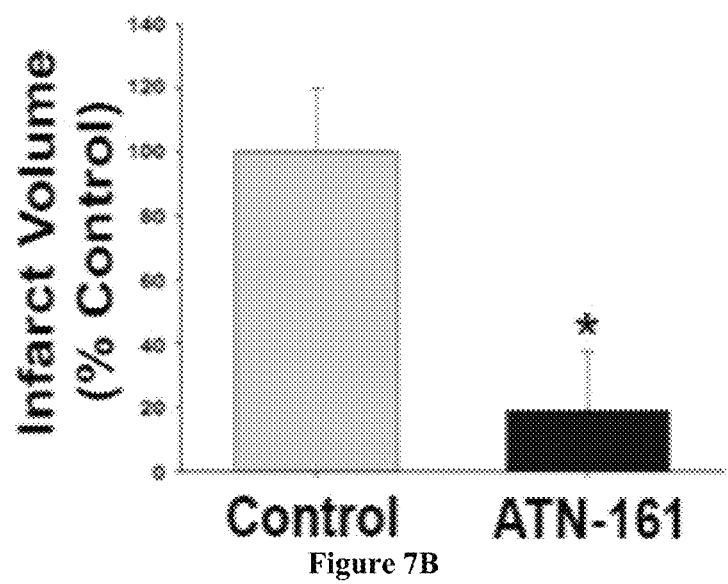
FIG. 7B includes a plot showing the quantification of mean infarct volume of the mice samples shown in FIG. 7A (expressed as a percent of control normalized to 100%). N=12, *P<0.05.
Figure 7C:
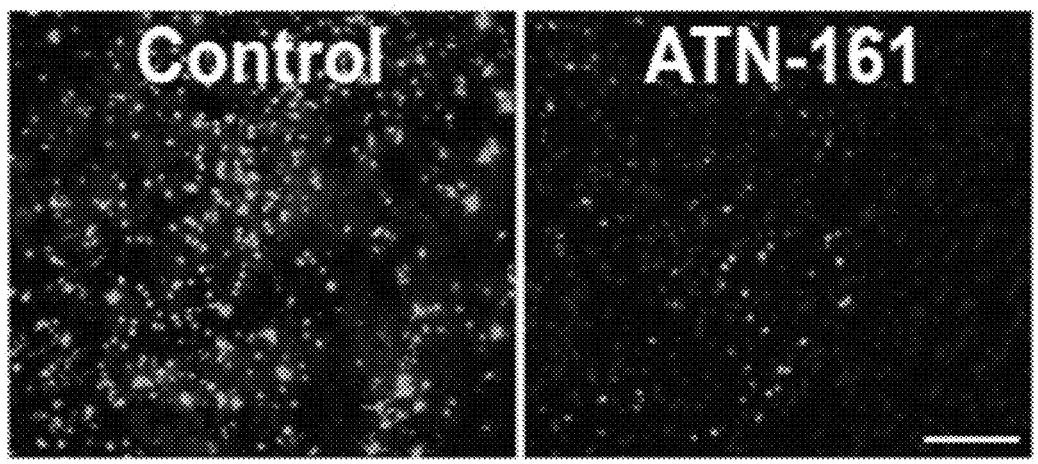
FIG. 7C includes images of TUNEL stain with DAPI nuclear counterstain showing stroke-affected brain areas on PSD3 as labeled, and demonstrating increased apoptosis in PBS treated versus ATN-161 treated mice. Scale bar is 50 μm.

To determine the therapeutic potential of blocking the α5β1 integrin after MCAo, 3 month old male WT mice were treated with ATN-161 or PBS vehicle control 12 hours after MCAo and assessed mean infarct volume and the extent of TUNEL positive apoptosis on PSD3 (FIGS. 7A to 7C, N=12, two separate experiments). ATN-161 treatment resulted in little to no TTC detected infarct and minimal apoptosis, supporting the notion that pharmacologically targeting the α5β1 integrin in stroked subjects can be therapeutic. Additionally, treatment with ATN-161 did not alter animal vital signs upon administration and was well tolerated, as indicated by a lack of signs of illness such as fur ruffling, weight differences, and the like.

Example 4

This Example describes procedures performed to characterize the role of α5β1 integrin in modulating blood-brain barrier integrity and subsequent resistance to ischemic stroke. Based on the results of the previous Examples that α5 integrin KO mice appear to resist post-stroke BBB breakdown after transient MCAo, and that post-stroke claudin-5 gene expression increases in these mice, it appears that suppression of brain endothelial cell α5β1 integrin in an ischemia-affected brain is neuroprotective, at least in part, by stabilization of the post-stroke BBB via increased expression and function of claudin-5.

Figure 8A:
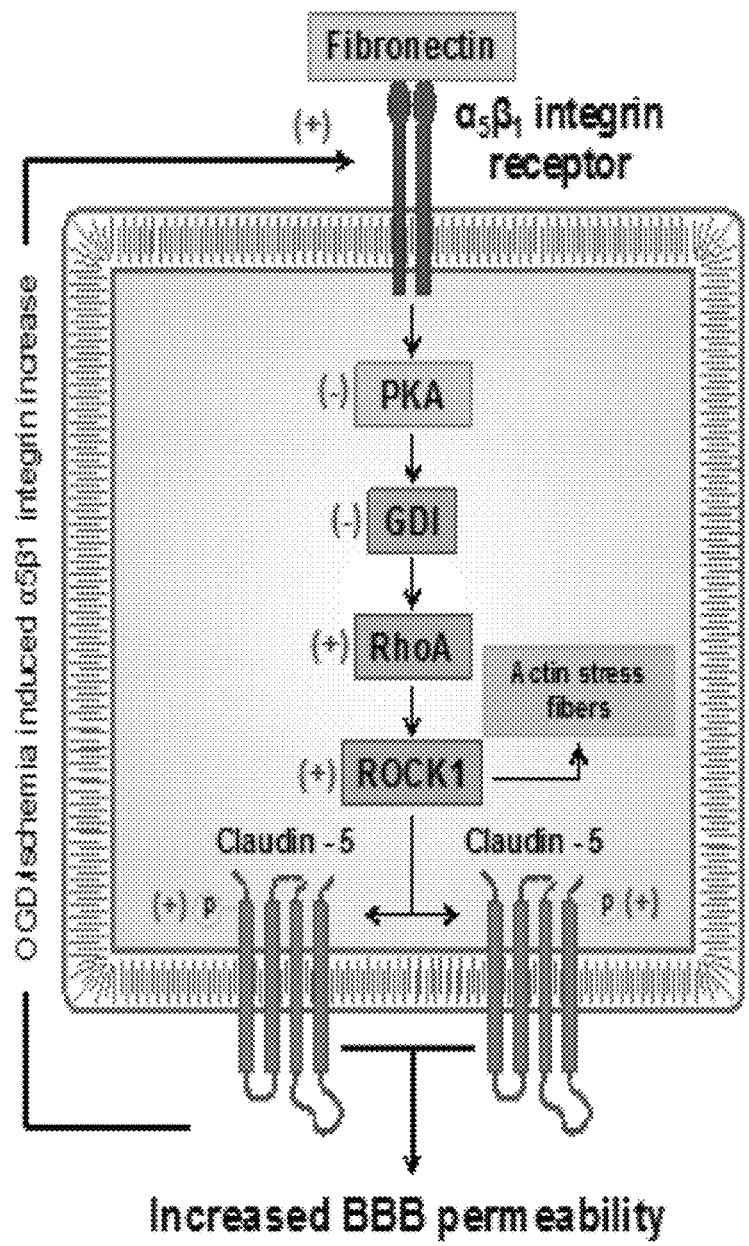
FIG. 8A includes a schematic showing that activation of α5β1 integrin by fibronectin increases inhibition of PKA, lowers levels of phosphorylation-mediated activation of GDI, increases levels of dissociated and active RhoA, increases activation of ROCK1, causes actin stress fiber rearrangement and phosphorylation of claudin-5 at position T207, creates a less tight junction integrity and increases BBB permeability, and subsequently leads to endothelial cell activation and increases α5β1 integrin expression.
Figure 8B:
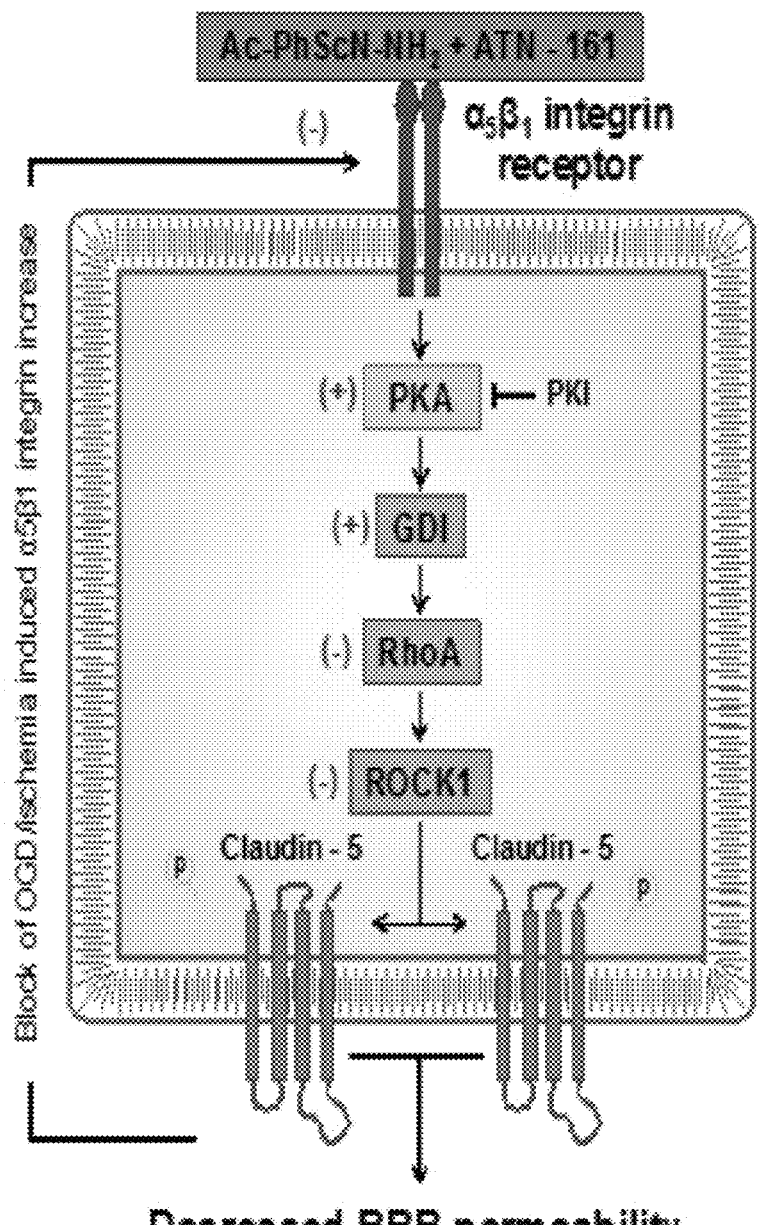
FIG. 8B includes a schematic showing that inhibition or absence of the α5β1 integrin prevents inhibition of PKA, increases phosphorylation-mediated activation of GDI, and creates no dissociation of RhoA as well as reduces ROCK1 activation, rearranges F-actin, and phosphorylizes claudin-5. This increases tight junction connections between endothelial cells decreases permeability and cellular activation, and prevents increase in α5β1 expression and endothelial cell activation.

Without being bound by theory or mechanism, claudin-5 stabilization, in addition to reducing paracellular permeability, could result in less cell surface expression of α5β1 integrin, less endothelial cell activation, and less transcellular permeability. Based on previous results, it appears that α5β1 is linked to protein kinase a (PKA), PKA to Ras homolog family member A (RhoA) and barrier stability effects, and RhoA to claudin-5 function via Rho-associated coiled-coil containing protein kinase 1 (ROCK1) mediated phosphorylation. Without being bound by theory or mechanism, a schematic for α5β1 mediation of tight junction (TJ) protein function and BBB permeability is summarized in FIGS. 8A and 8B.

Figure 9:
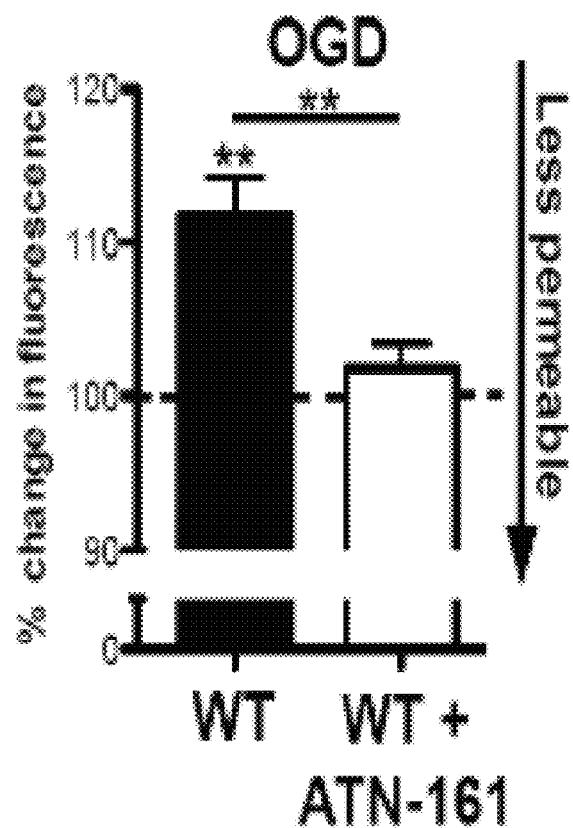
FIG. 9 includes a plot of post-OGD FITC-dextran permeability measurements across the monolayer of confluent (6 days) WT mouse brain endothelial cells exposed to OGD for 8 hours+/−ATN-161 (10 μM added 4 hours after OGD) and then returned to normoxic and normoglycemic conditions. Results shown as a percentage of pre-OGD FITC-dextran fluorescence in untreated WT cells, normalized to 100% (dashed line). **p<0.01. N=4.

To determine whether inhibition of α5β1 integrin with ATN-161 in brain endothelial cells has any effect on their permeability under baseline or stroke-like conditions (oxygen-glucose deprivation (OGD)-reperfusion) in vitro, FITC dextran permeability experiments were performed with a C57Bl6 WT brain endothelial cell line+/−ATN-161. While no differences were noted in FITC dextran permeability in non-OGD exposed cells+/−ATN-161 treatment (data not shown), ATN-161 blocked the OGD-mediated increase in endothelial cell permeability to FITC-dextran (FIG. 9). As the 8 hour OGD-24 hour reperfusion protocol did not cause significant endothelial cell death or detachment (trypan blue cell exclusion assay, data not shown), the ATN-161 effect on permeability cannot be simply attributed to potential OGD cell protection. This Example supports the notion that inhibition of brain endothelial cell α5β1 integrin stabilizes brain endothelial cell permeability under stroke-like (OGD-reperfusion) conditions.

Figure 10A:
FIG. 10A includes a Western blot for α5 integrin from WT mouse brain endothelial cells+/−ATN-161 before and after OGD as labeled.
Figure 10B:
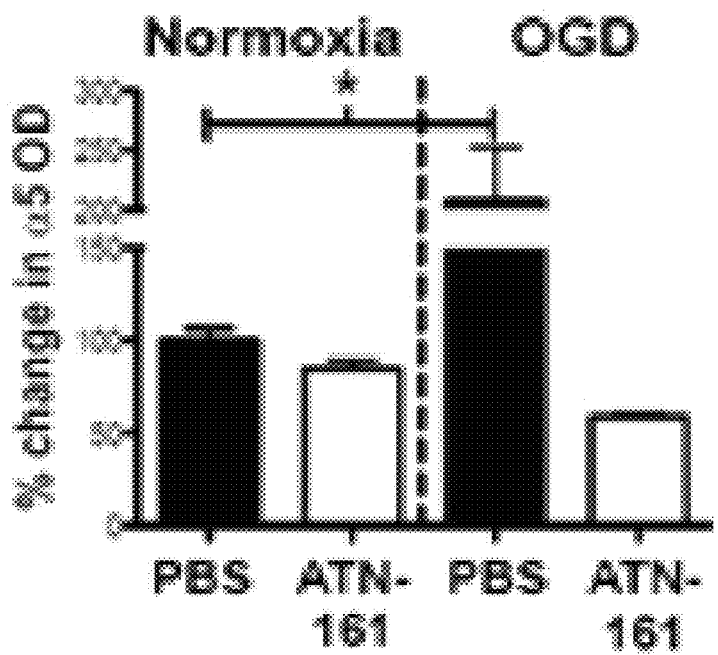
FIG. 10B includes a plot showing the quantification (mean values) of α5 western blots (as in FIG. 10A) normalized to Ponceau S. total protein stain and expressed as a % change from PBS treated pre-OGD cells. N=3. *p<0.05.

Next, it was determined that ATN-161 could block the OGD-induced increase in α5β1 integrin expression in WT brain endothelial cells (FIGS. 10A and 10B), supporting the notion that inhibiting α5β1 integrin might help stabilize brain endothelial cell permeability, in part, by preventing an increase in α5β1 integrin expression.

Figure 11A:
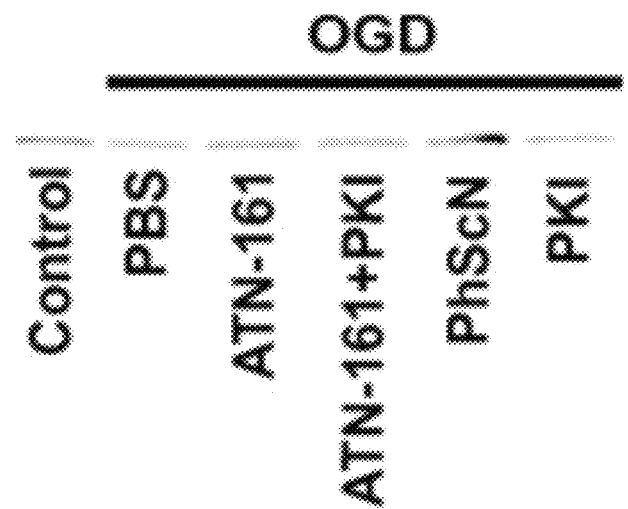
FIG. 11A includes a claudin-5 western blot of brain endothelial cells after OGD that were treated as labeled.
Figure 11B:
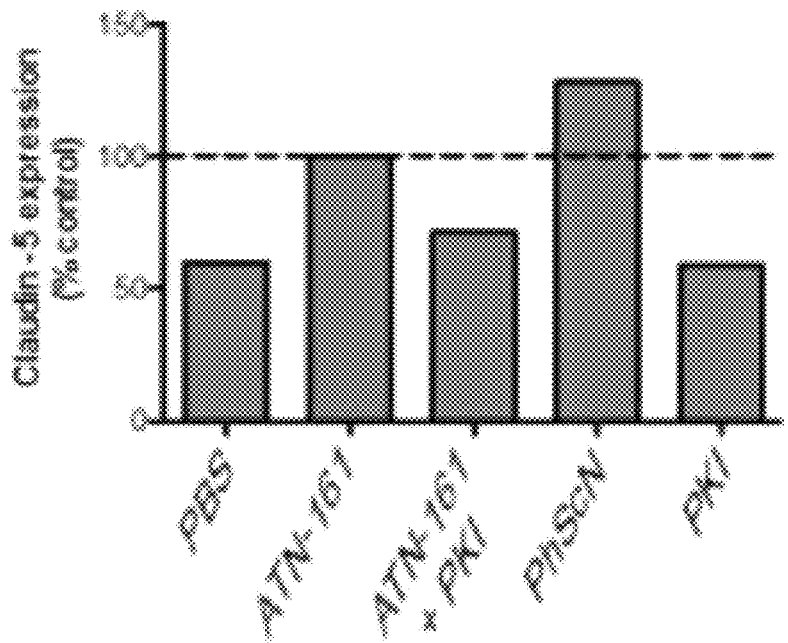
FIG. 11B includes plot showing the quantification of claudin-5 expression normalized to Ponceau S total protein stain for the samples show in FIG. 11A.
Figure 11C:
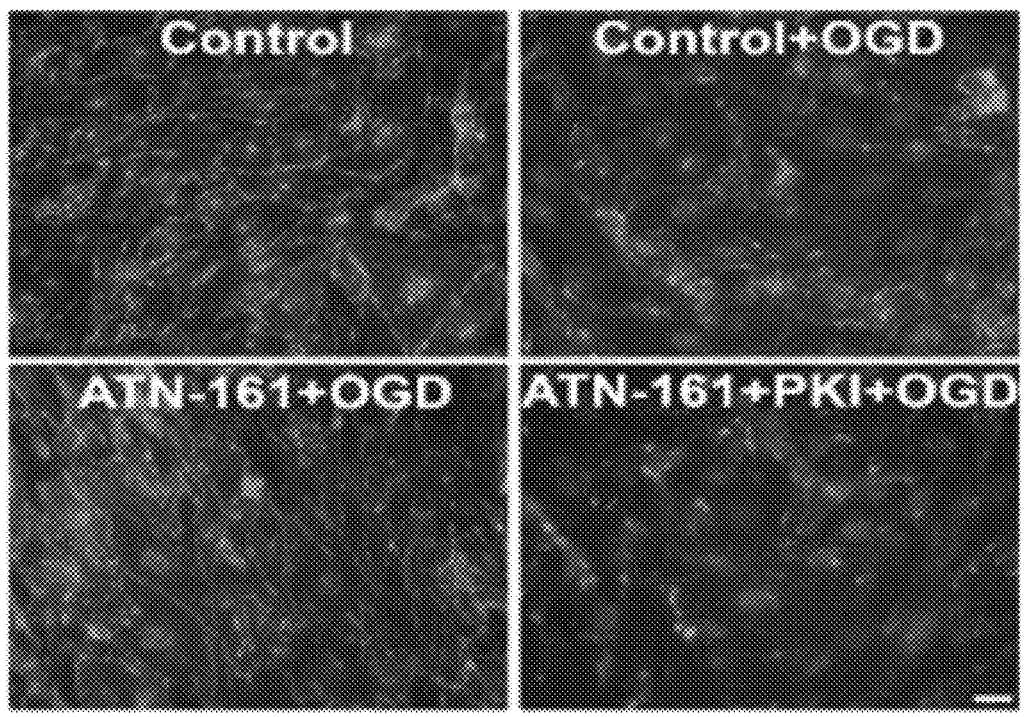
FIG. 11C includes images showing claudin-5 immunocytochemistry of WT mouse brain endothelial cells either just prior to (control) or 24 hours after OGD treated as labeled. Scale bar is 5 μm.

The studies also demonstrated that ATN-161 could prevent the OGD-mediated decrease in claudin-5 expression, as measured by western blot and immunocytochemistry, in mouse brain endothelial cells, which could be inhibited by the PKA specific inhibitor PKI (FIGS. 11A to 11C). It was noted that Ac-PhScN—NH2 was more effective than ATN-161 in further increasing claudin-5 levels above normoxic control levels.

Next, to demonstrate whether absent brain endothelial cell α5β1 integrin could affect claudin-5 expression after stroke, claudin-5 qPCR was performed on PSD1 from the stroked and sham cerebral hemispheres of α5 integrin KO mice and WT littermates. While sham claudin-5 levels were identical between the two genotypes, claudin-5 gene expression increased by 60% in stroked α5 integrin KO mice relative to stroked WT littermate controls, suggesting that endothelial cell knockdown of α5β1 integrin positively effects claudin-5 gene expression after ischemic stroke.

While the terms used herein are believed to be well understood by one of ordinary skill in the art, definitions are set forth herein to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "an inhibitor" includes a plurality of such inhibitors, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

Throughout this document, various references are mentioned. All such references are incorporated herein by reference.

REFERENCES

1. Sandoval K E, Witt K A. Blood-brain barrier tight junction permeability and ischemic stroke. *Neurobiology of Disease*. 2008; 32:200-219.
2. Hacke W, Kaste M, Fieschi C, et al. Intravenous thrombolysis with recombinant tissue plasminogen activator for acute hemispheric stroke: The european cooperative acute stroke study (ecass). *JAMA*. 1995; 274:1017-1025.
3. Hacke W, Kaste M, Fieschi C, von Kummer R, Davalos A, Meier D, et al. Randomised double-blind placebo-controlled trial of thrombolytic therapy with intravenous alteplase in acute ischaemic stroke (ecass ii). *The Lancet*. 1998; 352:1245-1251.
4. Clark W M, Wissman S, Albers G W, et al. Recombinant tissue-type plasminogen activator (alteplase) for ischemic stroke 3 to 5 hours after symptom onset: The atlantis study: A randomized controlled trial. *JAMA*. 1999; 282:2019-2026.
5. del Zoppo G J, Higashida R T, Furlan A J, Pessin M S, Rowley H A, Gent M. Proact: A phase ii randomized trial of recombinant pro-urokinase by direct arterial delivery in acute middle cerebral artery stroke. *Stroke*. 1998; 29:4-11.
6. Furlan A, Higashida R, Wechsler L, et al. Intra-arterial prourokinase for acute ischemic stroke: The proact ii study: A randomized controlled trial. *JAMA*. 1999; 282:2003-2011.
7. Investigators TIIT. The interventional management of stroke (ims) ii study. *Stroke*. 2007; 38:2127-2135.
8. Shireman T I, Howard P A, Kresowik T F, Ellerbeck E F. Combined anticoagulant-antiplatelet use and major bleeding events in elderly atrial fibrillation patients. *Stroke*. 2004; 35:2362-2367.
9. Lee B, Clarke D, Al Ahmad A, Kahle M, Parham C, Auckland L, et al. Perlecan domain v is neuroprotective and proangiogenic following ischemic stroke in rodents. *The Journal of Clinical Investigation*. 2011; 121:3005-3023.
10. Bix G J. Perlecan and the blood-brain barrier: Beneficial proteolysis? *Brain Res*. 2012; 3:155.
11. Saini M, Pinteaux E, Lee B, Bix G. Oxygen-glucose deprivation and interleukin-1a trigger the release of perlecan lg3 by cells of neurovascular unit. *J Neurochem*. 2011; 119:760-771.
12. Al-Ahmad A J, Lee B, Saini M, Bix G J. Perlecan domain v modulates astrogliosis in vitro and after focal cerebral ischemia through multiple receptors and increased nerve growth factor release. *Glia*. 2011; 59:1822-1840.
13. Bix G, Gowing E, Clarkson A. Perlecan domain v is neuroprotective and affords functional improvement in a photothrombotic stroke model in young and aged mice. *Translational Stroke Research*. 2013; 4:515-523.
14. Clarke D N, Al Ahmad A, Lee B, Parham C, Auckland L, Fertala A, et al. Perlecan domain v induces vegf secretion in brain endothelial cells through integrin α5b1 and erk-dependent signaling pathways. *PLOS ONE*. 2012; epub ahead of print: 445257.
15. Li L, Liu F, Welser-Alves J V, McCullough L D, Milner R. Upregulation of fibronectin and the α5β1 and αvβ3 integrins on blood vessels within the cerebral ischemic penumbra. *Experimental Neurology*. 2012; 233:283-291.
16. van der Flier A, Badu-Nkansah K, Whittaker C, Crowley D, Bronson R, Lacy-Hulbert A, et al. Endothelial alpha5 and alphav integrins cooperate in remodeling of the vasculature during development. *Development*. 2010; 137:2439-2449.
17. Li L, Welser-Alves J, van der Flier A, Boroujerdi A, Hynes R O, Milner R. An angiogenic role for the α5β1 integrin in promoting endothelial cell proliferation during cerebral hypoxia. *Experimental Neurology*. 2012; 237:46-54.
18. Maeda K, Hata R, Hossmann K. Differences in the cerebrovascular anatomy of c57black/6 and sv129 mice. *Neuroreport*. 1998; 9:1261-1265.
19. Yenari M A, Xu L, Tang X N, Qiao Y, Giffard R G. Microglia potentiate damage to blood-brain barrier constituents: Improvement by minocycline in vivo and in vitro. *Stroke*. 2006; 37:1087-1093.
20. Knowland D, Arac A, Sekiguchi Kohei J, Hsu M, Lutz Sarah E, Perrino J, et al. Stepwise recruitment of transcellular and paracellular pathways underlies blood-brain barrier breakdown in stroke. *Neuron*. 2014; 82:603-617.

21. Ishida J, Onishi M, Kurozumi K, Ichikawa T, Fujii K, Shimazu Y, et al. Integrin inhibitor suppresses bevacizumab-induced glioma invasion. *Translational Oncology.* 2014; 7:292-302.e291.
22. Livant D L, Brabec R K, Pienta K J, Allen D L, Kurachi K, Markwart S, et al. Anti-invasive, antitumorigenic, and antimetastatic activities of the phscn sequence in prostate carcinoma. *Cancer Research.* 2000; 60:309-320.
23. Cianfrocca M E, Kimmel K A, Gallo J, Cardoso T, Brown M M, Hudes G, et al. Phase 1 trial of the antiangiogenic peptide atn-161 (ac-phscn-nh2), a beta integrin antagonist, in patients with solid tumours. *Br J Cancer.* 2006; 94:1621-1626.
24. Khalili P, Arakelian A, Chen G, Plunkett M L, Beck I, Parry G C, et al. A non-rgd-based integrin binding peptide (atn-161) blocks breast cancer growth and metastasis in vivo. *Molecular Cancer Therapeutics.* 2006; 5:2271-2280.
25. Doñate F, Parry G C, Shaked Y, Hensley H, Guan X, Beck I, et al. Pharmacology of the novel antiangiogenic peptide atn-161 (ac-phscn-nh2): Observation of a u-shaped dose-response curve in several preclinical models of angiogenesis and tumor growth. *Clinical Cancer Research.* 2008; 14:21372144.
26. Wang W, Wang F, Lu F, Xu S, Hu W, Huang J, et al. The antiangiogenic effects of integrin $\alpha5\beta1$ inhibitor (atn-161) in vitro and in vivo. *Investigative Ophthalmology & Visual Science.* 2011; 52:72137220.
27. Veine D, Yao H, Stafford D, Fay K, Livant D. A d-amino acid containing peptide as a potent, noncovalent inhibitor of $\alpha5\beta1$ integrin in human prostate cancer invasion and lung colonization. *Clinical & Experimental Metastasis.* 2014; 31:379-393.
28. Shimamura N, Matchett G, Solaroglu I, Tsubokawa T, Ohkuma H, Zhang J. Inhibition of integrin $\alpha v\beta3$ reduces blood-brain barrier breakdown in focal ischemia in rats. *Journal of Neuroscience Research.* 2006; 84:1837-1847.
29. Shimamura N, Matchett G, Yatsushige H, Calvert J W, Ohkuma H, Zhang J. Inhibition of integrin $\alpha v\beta3$ ameliorates focal cerebral ischemic damage in the rat middle cerebral artery occlusion model. *Stroke.* 2006; 37:1902-1909.
30. Osada T, Gu Y-H, Kanazawa M, Tsubota Y, Hawkins B T, Spatz M, et al. Interendothelial claudin-5 expression depends on cerebral endothelial cell-matrix adhesion by [beta]1-integrins. *J Cereb Blood Flow Metab.* 2011; 31:1972-1985.
31. Lathia J D, Chigurupati S, Thundyil J, Selvaraj P K, Mughal M R, Woodruff T M, et al. Pivotal role for beta-1 integrin in neurovascular remodelling after ischemic stroke. *Experimental Neurology.* 2010; 221:107114.
32. Diener H C, Lees K R, Lyden P, Grotta J, Davalos A, Davis S M, et al. Nxy-059 for the treatment of acute stroke: Pooled analysis of the saint i and ii trials. *Stroke.* 2008; 39:1751-1758.
33. Saito I, Segawa H, Shiokawa Y, Taniguchi M, Tsutsumi K. Middle cerebral artery occlusion: Correlation of computed tomography and angiography with clinical outcome. *Stroke.* 1987; 18:863-868.
34. Bix G, Gowing E, Clarkson A. Perlecan domain v is neuroprotective and affords functional improvement in a photothrombotic stroke model in young and aged mice. *Translational Stroke Research.* 2013:1-9.
35. Carmichael S. Rodent models of focal stroke; size, mechanism, and purpose. *NeuroRx.* 2005; 2:396409.
36. Bix G J. Perlecan domain v is neuroprotective and affords functional improvement in a photothrombotic stroke model in young and aged mice. *Trans Stroke Res.* 2013; 4:515-523.
37. Lo E H. A new penumbra: Transitioning from injury into repair after stroke. *Nat Med.* 2008; 14:497-500.
38. Kasirer-Friede A, Kahn M L, Shattil S J. Platelet integrins and immunoreceptors. *Immunological Reviews.* 2007; 218:247-264.
39. Hayon Y, Dashevsky 0, Shai E, Varon D, Leker R R. Platelet lysates stimulate angiogenesis, neurogenesis and neuroprotection after stroke. *Thrombosis and Haemostasis.* 2013; 110:323-330.
40. Danese S, Sans M, Spencer D M, Beck I, Doñate F, Plunkett M L, et al. Angiogenesis blockade as a new therapeutic approach to experimental colitis. *Gut.* 2007; 56:855-862.
41. Uniyal S, Boeters L, Chakrabarti S, Singh B, Chan B M C. Leukocytes utilize both $\alpha4$ and $\alpha5$ integrins for intraislet infiltration in non-obese diabetic mice. *Journal of Autoimmunity.* 1999; 12:167-176.
42. Langhauser F, Kraft P, Gob E, Leinweber J, Schuhmann M K, Lorenz K, et al. Blocking of $\alpha4$ integrin does not protect from acute ischemic stroke in mice. *Stroke.* 2014.
43. Dahlman J E, Barnes C, Khan O, Thiriot A, Jhunjunwala S, Shaw T E, et al. In vivo endothelial sirna delivery using polymeric nanoparticles with low molecular weight. *Nat Nano.* 2014; advance online publication.
44. Chen L, Swartz K R, Toborek M. Vessel microport technique for applications in cerebrovascular research. *Journal of Neuroscience Research.* 2009; 87:1718-1727.
45. Kim S, Bakre M, Yin H, Varner J A Inhibition of endothelial cell survival and angiogenesis by protein kinase a. *J. Clin. Inv.* 2002; 110:933-941.
46. Qiao J, Huang F, Lum H. *Pka inhibits rhoa activation: A protection mechanism against endothelial barrier dysfunction.* 2003.
47. Persidsky Y, Heilman D, Haorah J, Zelivyanskaya M, Persidsky R, Weber G A, et al. Rho-mediated regulation of tight junctions during monocyte migration across the blood-brain barrier in hiv-1 encephalitis (hive). *Blood.* 2006; 107:4770-4780.
48. Yamamoto M, Ramirez S H, Sato S, Kiyota T, Cerny R L, Kaibuchi K, et al. Phosphorylation of claudin-5 and occludin by rho kinase in brain endothelial cells. *The American Journal of Pathology.* 2008; 172:521-533.
49. Al Ahmad A, Gassman M, Ogunshola O. Maintaining blood-brain barrier integrity: Pericytes perform better than astrocytes during prolonged oxygen deprivation. *J Cell Physiol.* 2009; 218:612-622.
50. Bix G, Fu J, Gonzalez E, Macro L, Barker A, Campbell S, et al. Endorepellin causes endothelial cell disassembly of actin cytoskeleton and focal adhesions through the $\alpha2\beta1$ integrin. *J. Cell Biol.* 2004; 166:97-109.
51. Glass D B, Lundquist L J, Katz B M, Walsh D A. Protein kinase inhibitor-(6-22)-amide peptide analogs with standard and nonstandard amino acid substitutions for phenylalanine 10. Inhibition of camp-dependent protein kinase. *Journal of Biological Chemistry.* 1989; 264:14579-14584.
52. Saini M G, Bix G J. Oxygen-glucose deprivation (ogd) and interleukin-1 (il-1) differentially modulate cathepsin b/1 mediated generation of neuroprotective perlecan lg3 by neurons. *Brain Research.* 2012; 1438:65-74.
53. Brooks T A, Hawkins B T, Huber J D, Egleton R D, Davis T P. Chronic inflammatory pain leads to increased blood-brain barrier permeability and tight junction protein alterations. *American Journal of Physiology—Heart and Circulatory Physiology.* 2005; 289:H738-H743.
54. Yousif S, Marie-Claire C, Roux F, Schumann J-M, Declèves X. Expression of drug transporters at the blood-brain barrier using an optimized isolated rat brain microvessel strategy. *Brain Research.* 2007; 1134:1-11.
55. Abbott N J. Blood-brain barrier structure and function and the challenges for cns drug delivery. *J Inherit Metab Dis.* 2013; 36:437-449.
56. Hofmann F, Dostmann W, Keilbach A, Landgraf W, Ruth P. Structure and physiological role of cgmp-dependent protein kinase. *Biochimica et Biophysica Acta (BBA)—Molecular Cell Research.* 1992; 1135:51-60.

What is claimed is:

1. A method for treating ischemia in a subject, comprising: administering to a subject in need thereof an effective amount of a α5β1 integrin inhibitor thereby treating the ischemia, wherein the ischemia is caused by an ischemic event selected from cerebral ischemia and/or stroke, and wherein the α5β1 integrin inhibitor is ATN-161 or Ac-PhScN—NH$_2$.

2. The method of claim 1, wherein the α5β1 integrin inhibitor is administered during or after the onset of the ischemia.

3. The method of claim 1, wherein the α5β1 integrin inhibitor is administered about 0.5 hours to about 30 hours after the onset of the ischemia.

4. The method of claim 1, wherein the α5β1 integrin inhibitor is administered prior to the onset of ischemia.

5. The method of claim 1, wherein the treatment prevents the occurrence of an infarction.

6. The method of claim 1, wherein the treatment restores perfusion to organs and tissues.

7. The method of claim 1, wherein the administering step includes administering about 1 mg/kg to about 50 mg/kg of the α5β1 integrin inhibitor.

8. A method for preventing an infarction caused by a cerebral ischemia event in a subject, comprising: administering to a subject in need thereof an effective amount of a α5β1 integrin inhibitor thereby preventing the infarction, wherein prior to the step of administering the α5β1 integrin inhibitor, the subject is diagnosed as having cerebral ischemia, and wherein the α5β1 integrin inhibitor is ATN-161 or Ac-PhScN—NH$_2$.

9. The method of claim 8, wherein the α5β1 integrin inhibitor is administered during, or after the cerebral ischemic event.

10. The method of claim 9, wherein the α5β1 integrin inhibitor is administered about 0.5 to about 30 hours after the cerebral ischemic event.

11. The method of claim 8, wherein about 5% to about 95% of infarction is prevented in the subject relative to a control subject.

12. The method of claim 8, wherein the administering step includes administering about 1 mg/kg to about 50 mg/kg of the α59β1 integrin inhibitor.

* * * * *